United States Patent [19]
Ohlsson

[11] 4,023,565
[45] May 17, 1977

[54] CIRCUIT ARRANGEMENT FOR THE PROCESSING OF PHYSIOLOGICAL MEASURING SIGNALS

[75] Inventor: Thomas Ohlsson, Vallingby, Sweden

[73] Assignee: Siemens Aktiengesellschaft, Berlin & Munich, Germany

[22] Filed: June 19, 1975

[21] Appl. No.: 588,467

[30] Foreign Application Priority Data

June 21, 1974 Germany .......................... 2429953

[52] U.S. Cl. .......................................... 128/2.06 B
[51] Int. Cl.² ......................................... A61B 5/04
[58] Field of Search ................. 128/2.06 B, 2.06 G, 128/2.06 R, 2.1 R

[56] References Cited

UNITED STATES PATENTS

| | | | |
|---|---|---|---|
| 3,709,212 | 1/1973 | Koeblitz .......................... | 128/2.06 B |
| 3,811,428 | 5/1974 | Van Horn et al. ............. | 128/2.06 B |

OTHER PUBLICATIONS

Huntsman et al., "IEEE Transactions on Bio-Medical Engineering" vol. 18, No. 4, July, 1971 pp. 301–302.
Duffin, Jr., et al., "Proceedings of the 23rd Annual Conference on Engineering In Medicine & Biology", Washington D.C. Nov. 16–19, 1970 p. 193.

*Primary Examiner*—William E. Kamm
*Attorney, Agent, or Firm*—Hill, Gross, Simpson, Van Santen, Steadman, Chiara & Simpson

[57] ABSTRACT

A circuit arrangement for the processing of physiological measuring signals, in which there is provided a plurality of input amplifiers each having a positive and a negative input, whose output signals control a signal reproducing arrangement, and which are each connected to a collector electrode. Connected to the positive inputs of the input amplifier are the collector electrodes for the signals, and that resistors are located between the negative inputs and the outputs of the input amplifiers, the negative inputs being connected across resistors with a common potential junction, and that the two inputs of a differential amplifier are connected to the outputs of respectively two input amplifiers, the output signal of the differential amplifier controlling the signal reproducing arrangement, and in which the common potential junction is connected to the collector electrode.

5 Claims, 3 Drawing Figures

CIRCUIT ARRANGEMENT FOR THE PROCESSING OF PHYSIOLOGICAL MEASURING SIGNALS

FIELD OF THE INVENTION

The present invention relates to a circuit arrangement for the processing of physiological measuring signals.

DISCUSSION OF THE PRIOR ART

Presently known is a circuit arrangement for the processing of physiological measuring signals, namely, an electrocardiograph, in which there is provided a plurality of input amplifiers each having a positive and a negative input, whose output signals control a signal reproducing arrangement, and which are each connected to a collector electrode.

In the known electrocardiographs, all of the voltages which are branched or tapped off from a patient are measured in comparison with a voltage which is tapped off from a reference electrode. In that manner, there is achieved that interference signals (static hum) which cause the potential of the entire body to deviate from zero, are extensively eliminated. The exclusion of these static signals is effectuated in that the input amplifiers are constructed as differential amplifiers which amplify the difference between their present input signal and the reference signal, and wherein the static hum is also impressed or superimposed on the input signal as an in-phase signal.

A satisfactory operating effect is afforded in the known electrocardiographs only when the input amplifiers all possess the same definite amplification and when, in particular, the components of these amplifiers evidence relatively narrow tolerances so that, upon subtraction of two equally large input signals of a differential amplifier, there is obtained the output signal zero with a high degree of exactness. A disadvantage in the known electrocardiographs lies in that the circuit requirements or expenditures for the input amplifiers are quite considerable.

SUMMARY OF THE INVENTION

Accordingly, it is an object of the present invention to provide a circuit arrangement of the above-mentioned type, in which the input circuit is essentially more simply constructed than those in the current state of the technology wherein, particularly in this circuit, utilization is made of operational amplifiers, and in which tolerances in the components which are within relatively wide limits will not adversely affect the in-phase suppression, meaning the suppression of interference or static signals. Furthermore, even at times when one or more collector or take-off electrodes are not connected, which may occur in the obtention of EKG or EEG, there is afforded a satisfactory in-phase suppression, meaning, suppression of interference signals.

The foregoing object is inventively achieved in that connected to the positive inputs of the input amplifier are the collector electrodes for the signals, and that resistors are located between the negative inputs and the outputs of the input amplifiers, the negative inputs being connected across resistors with a common potential junction, and that the two inputs of a differential amplifier are connected to the outputs of at least two input amplifiers, the output signal of the differential amplifier controlling the signal reproducing arrangement, and in which the common potential junction is connected with a take-off electrode. In the inventive circuit arrangement, each input amplifier may be constructed of a commercially available operational amplifier which is wired with two additional resistors. The construction of an input amplifier is thus appreciably simplified in comparison with those in the current state of the art. The tolerances of these resistors and their amplification of the input amplifiers exert no effect on the extent of the in-phase suppression. The suppression is carried out by means of a differential amplifier which is connected to the input amplifiers. The in-phase suppression within the entire arrangement, however, is dependent upon the internal in-phase suppression of the amplifier in the input circuit. The in-phase signals are not amplified by means of the input amplifiers, whereas the differential signals between two electrodes appear amplified at the outputs of the input amplifiers, so that tolerances of the thereto connected differential amplifier are effective on the in-phase suppression reduced by only the amplification factor. In the inventive circuit arrangement, the interference signal of one input channel, is impressed on the collective input amplifiers as the interference signal, so that the output signals of the input amplifiers which incorporate the interference signals are all equal, and are eliminated in the difference formation in the additionally connected differential amplifiers. It is important in the utilization of the inventive circuit arrangement that the particular collector electrode which is connected to the common potential junction is applied to the body of the patient.

BRIEF DESCRIPTION OF THE DRAWINGS

Further advantages and details of the invention may now be ascertained from the following description of exemplary embodiments thereof, taken in conjunction with the accompanying drawing which illustrates circuit arrangements pursuant to the invention and in which.

DETAILED DESCRIPTION

Figure 1:
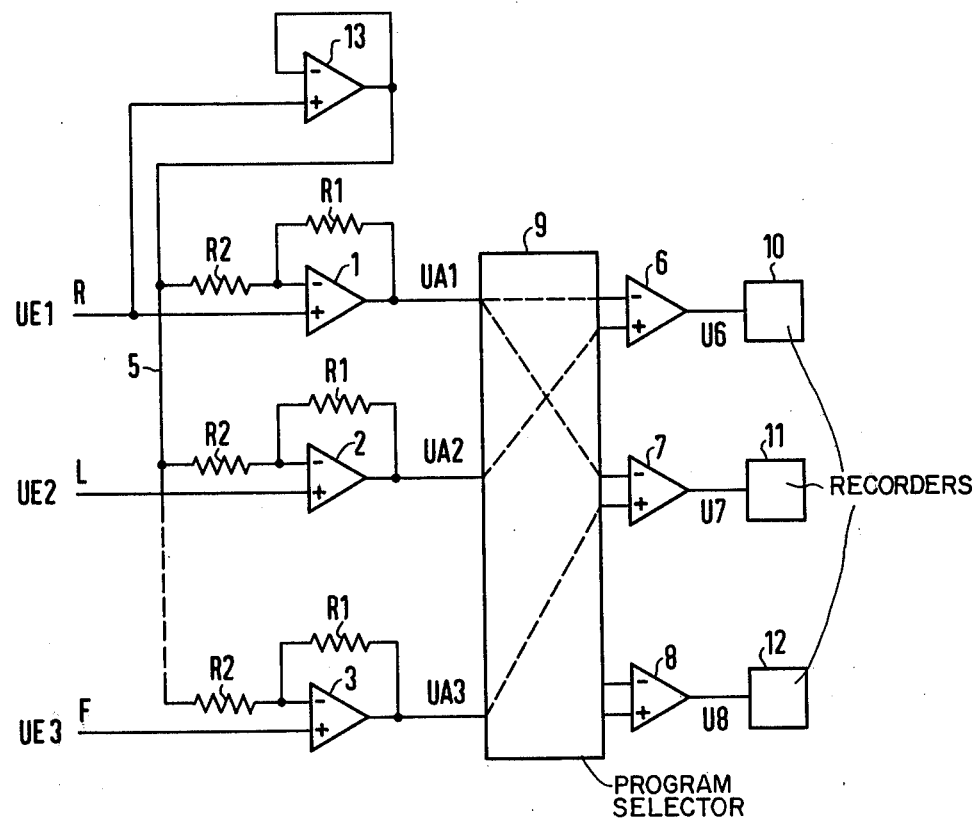
FIG. 1 is a schematic diagram of an exemplary embodiment of the present invention.

The illustrated exemplary embodiment of FIG. 1 serves for the obtention of an EKG. Provided are three operational amplifiers 1 to 3 having three collector or take-off electrodes R, L and F connected to the respective positive inputs thereof. The electrode R is applied to the right arm of the patient, the electrode L to the left arm, and the electrode F to one foot. The phantom lines in the drawing indicate that still further electrodes are present, each of which having an additional operational amplifier associated therewith. The negative inputs of the operational amplifiers 1 to 3 are connected to their outputs through resistors R1, and connected through resistors R2 with a common potential junction 5. The operational amplifiers possess a high degree of amplification in a non-feedback connected condition, as well as a high input impedance and a low output impedance. There is thus ascertained that the in-phase signals (interference signals) at the inputs of the operational amplifiers 1 through 3 again reappear unchanged at their outputs, whereas the differential signal between the outputs signals of two operational amplifiers, in comparison with the differential signals between the corresponding input signals, are amplified by the factor 1 + R1/R2.

The outputs of the operational amplifiers 1 through 3 are connected with differential amplifiers 6 through 8 through a program selector 9 in accordance with a predetermined program. The differential amplifier 6, for example, forms the difference from the output signals of the operational amplifiers 1 and 2. During the difference formation, the interference signals are eliminated, while the difference signals between the input signals, for example, between the signals R and L, are obtained amplified by the factor 1 + R1/R2. The differential amplifiers 6 through 8 control EKG reproducing installations 10 through 12 which, for example, may be recorders as described in Canadian Pat. No. 513,848.

The common potential junction 5 is located at the output of a voltage follower amplifier or impedance transformer 13 whose positive input is connected with the potential which is tapped-off by the electrode R. The voltage follower amplifier 13 has a voltage amplification of 1 : 1, a low output impedance and a high input impedance. The voltage follower amplifier also has the effect that, when one of the electrodes L and F is not connected to the patient, the same in-phase voltage is encountered at the outputs of all operational amplifiers. During the difference formation in the differential amplifiers 6, 7 and 8, there is eliminated the interference signal. A circuit arrangement, according to FIG. 1 of the drawing, also facilitates that there also be taken an EKG when not all of the collector electrodes are connected to the patient whereby, also in this instance, the interference signals are suppressed.

For the output voltages, the following pertains at R1/R2 = 30:

UA1 = (UE1 − UE1) . 30 + UE1 = UE1
UA2 = (UE2 − UE1) . 30 + UE2 = 31UE2 − 30UE1
UA3 = (UE3 − UE1) . 30 + UE3 = 31UE3 − 30UE1

For the output signal of differential amplifier 6, for example, the following is applicable: U6 = 31UE2 − 31UE1 = 31 . (UE2 − UE1). For the output signal U7, for example, the following is applicable: U7 = 31 . (UE3 − UE1).

With respect to the static hum it is applicable that UE1 = UE2 = UE3, since the static voltage is equally large at all three inputs. Substituting for the static voltage U, then for the static voltage the following is applicable:

UA1 = UA2 = UA3 = (U − U) . 30 + U = U.

Whereas the static voltage in the input circuits is not amplified and is eliminated through intermediary of the differential amplifiers, the differential signals are amplified by the factor 31. Tolerances in the amplification of the operational amplifiers 1 through 3, as well as tolerances of the resistors R1 and R2 exert no effect on the suppression of the interference signals.

It is essential for the circuit arrangement that always the same electrode which is connected to the voltage amplifier 13 (R), is applied to the patient.

The inventive circuit arrangement is universally applicable to the processing of physiological measuring signals, for example, it is also applicable for an EEG.

Figure 2:
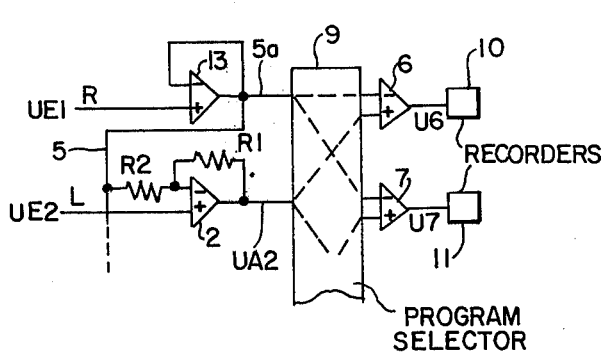
FIG. 2 illustrates a first modification of the embodiment of FIG. 1.
Figure 3:
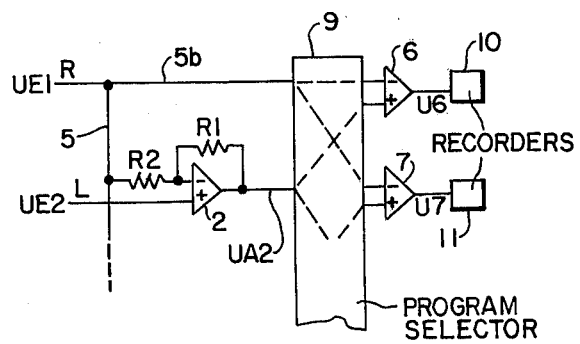
FIG. 3 illustrates a further modification of the embodiment of FIG. 1.

From the above branching off or dividing of the output voltages there is thus ascertained that the output voltage UA1 = UE1. Within the scope of the invention, the operational amplifier 1 may accordingly be eliminated (as shown in FIG. 2) when the output signal of the voltage amplifier 13 is transmitted to the program selector 9 via line 5a, FIG. 2, and thereby directly transmitted to one input of the differential amplifier 6. When the voltage amplifier 13 is not present (as shown in FIG. 3), then the signal (UE1) which is tapped-off from the electrode R, can be directly transmitted to the program selector 9 via line 5b, FIG. 3. It is thus important for these two cases that the potential of the common potential junction 5 be transmitted directly to the input of one or more differential amplifiers; in the present example, the differential amplifiers 6 and 7 (as shown in FIGS. 2 and 3). In the illustrated example of FIG. 1, the operational amplifier 1 is provided for reasons of symmetry. Deviations of the potential from UE1 at the common potential junction 5, also in this instance hardly effect themselves as disturbing.

In summation, it may be ascertained as being essential to the manner of operation of the circuit arrangement pursuant to FIG. 1 of the drawing that, independently as to whether the electrodes L and F are or are not connected to the patient, the outputs of all operational amplifiers 1 to 3 assume the same interference voltage in relation to the ground reference, as does the input of the operational amplifier 1 which is connected with voltage amplifier 13, in effect, as does the negative input of the operational amplifier 1. During the formation of the differential between the two output voltages, the interference signal is accordingly always eliminated.

The above branching off of the output voltages of the operational amplifiers 1 through 3 is obtained in that an operational amplifier with the associated resistors R1 and R2 may be produced in an equivalent circuit diagram by means of a differential amplifier with an additionally connected adding element which adds the output voltage of the differential amplifier to the input voltage received from the corresponding electrode.

While there has been shown what is considered to be the preferred embodiment of the invention, it will be obvious that modifications may be made which come within the scope of the disclosure of the specification.

What is claimed is:

1. In a circuit arrangement for the processing of physiological measuring signals, including a plurality of input amplifiers each having respectively a positive input and a negative input; a signal reproducing installation; and a take-off electrode connected to each amplifier, said take-off electrodes for said signals being connected to the positive inputs of said input amplifiers; first resistors being connected between said negative inputs and the outputs of said input amplifiers; second resistors connected between said negative inputs and a potential junction common to all input amplifiers; and a differential amplifier having two inputs connected to the outputs of each two of said input amplifiers, the output of said differential amplifier being connected to said signal reproducing installation, said differential amplifier providing an output signal for controlling said signal reproducing installation, a program selector connected between the outputs of said input amplifiers and the inputs of the differential amplifier for connecting pre-programmed output pairs of the input amplifiers to said differential amplifier, said common potential junction being connected to a take-off electrode free of ground potential.

2. A circuit arrangement as claimed in claim 1, comprising an impedance transformer connected between said last-mentioned take-off electrode and said common potential junction, said impedance transformer having a voltage amplification of 1, a high input resistance and a low output resistance.

3. A circuit arrangement as claimed in claim 1, said take-off electrodes comprising EKG-electrodes.

4. A circuit arrangement as claimed in claim 1, comprising means for directly transmitting the potential of said common potential junction to the input of at least one said differential amplifier.

5. A circuit arrangement as claimed in claim 1, each said input amplifier comprising an operational amplifier.

* * * * *